US00PP15949P2

(12) United States Plant Patent
Boeder

(10) Patent No.: US PP15,949 P2
(45) Date of Patent: Sep. 13, 2005

(54) ***CHRYSANTHEMUM* PLANT NAMED 'KIKO'**

(50) Latin Name: *Chrysanthemum morifolium*
Varietal Denomination: Kiko

(75) Inventor: Mark Roland Boeder, The Hague (NL)

(73) Assignee: Chrysanthemum Breeders Association, N.V. (NL)

( * ) Notice: Subject to any disclaimer, the term of this patent is extended or adjusted under 35 U.S.C. 154(b) by 117 days.

(21) Appl. No.: 10/782,773

(22) Filed: Feb. 23, 2004

(51) Int. Cl.[7] ..... A01H 5/00
(52) U.S. Cl. ..... Plt./291
(58) Field of Search ..... Plt./291

*Primary Examiner*—Anne Marie Grunberg
(74) *Attorney, Agent, or Firm*—Parkhurst & Wendel, L.L.P.

(57) ABSTRACT

A *Chrysanthemum* plant named 'Kiko', which when grown as a disbud is characterized by large inflorescences, about 19 cm in diameter, with elongated quilled pink ray-florets, with response time of 56 days.

3 Drawing Sheets

BACKGROUND OF THE INVENTION

'Kiko' is a product of a breeding-program which had the objective of creating new *Chrysanthemum* cultivars with a decorative type flower, a 8 week response and a medium plant height (1 m.). The new plant of the present invention comprises a new and distinct cultivar of *Chrysanthemum* plant. 'Kiko' is a seedling from a cross in a breeding program maintained under the control of inventor. The female parent is #98.0106-unpatented-, an unnamed seedling not available to inventor for description. The male parent is unknown, being a mixed population of a group of male parents. The new and distinct cultivar was discovered and selected as a flowering plant within the progeny of the stated cross by Mark Roland Boeder in a controlled environment (greenhouse) in Rijsenhout Holland in 2001. The first act of asexual reproduction of 'Kiko' was accomplished when vegetative cuttings were taken and propagated from the initial selection in 2001 in a controlled environment in Rijsenhout Holland.

SUMMARY OF THE INVENTION

The present invention is a new and distinct variety of *Chrysanthemum* bearing spectacularly large blooms with elongated quilled pink ray-florets.

BRIEF DESCRIPTION OF THE DRAWINGS

The present invention of a new and distinct variety of *Chrysanthemum* is shown in the accompanying drawings, the color being as nearly true as possible with color photographs of this type.

DESCRIPTION OF THE INVENTION

Figure 1:
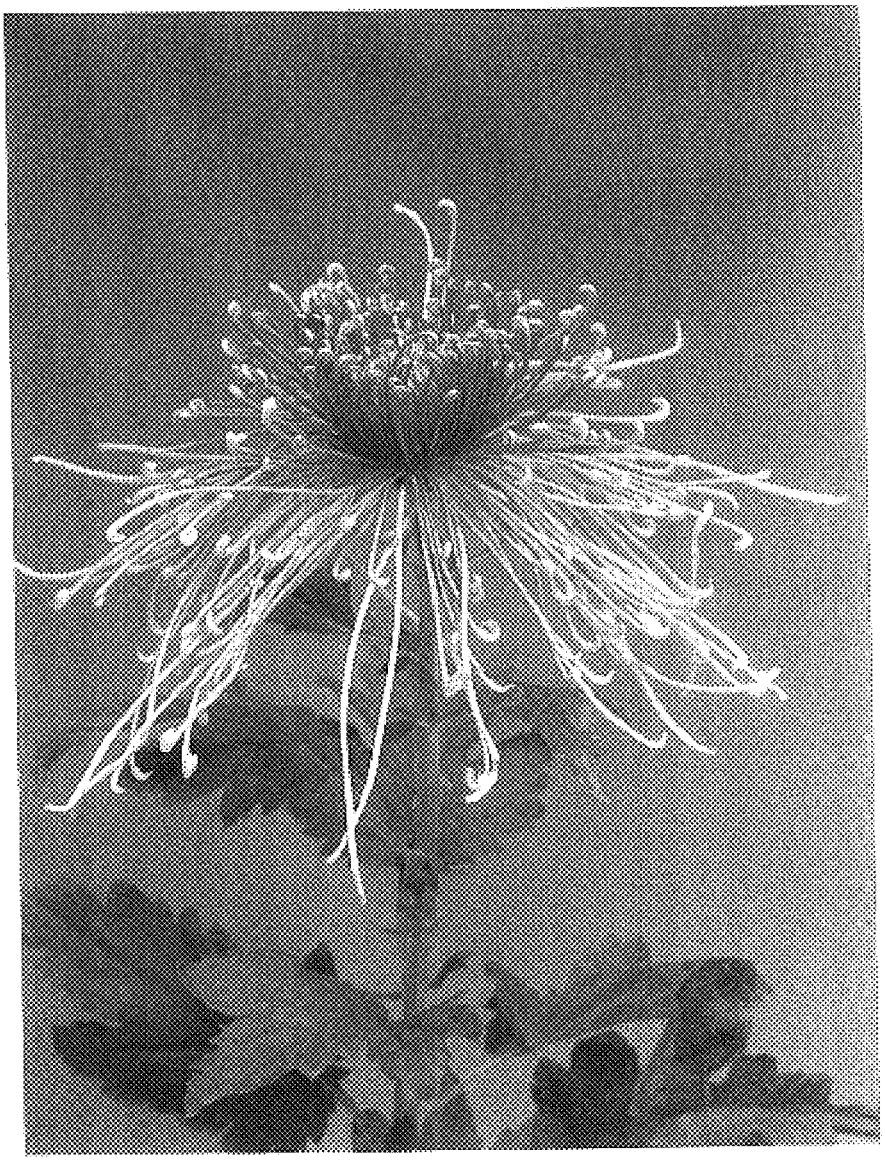
FIG. 1 shows a plant of the cultivar in full bloom.
Figure 2:
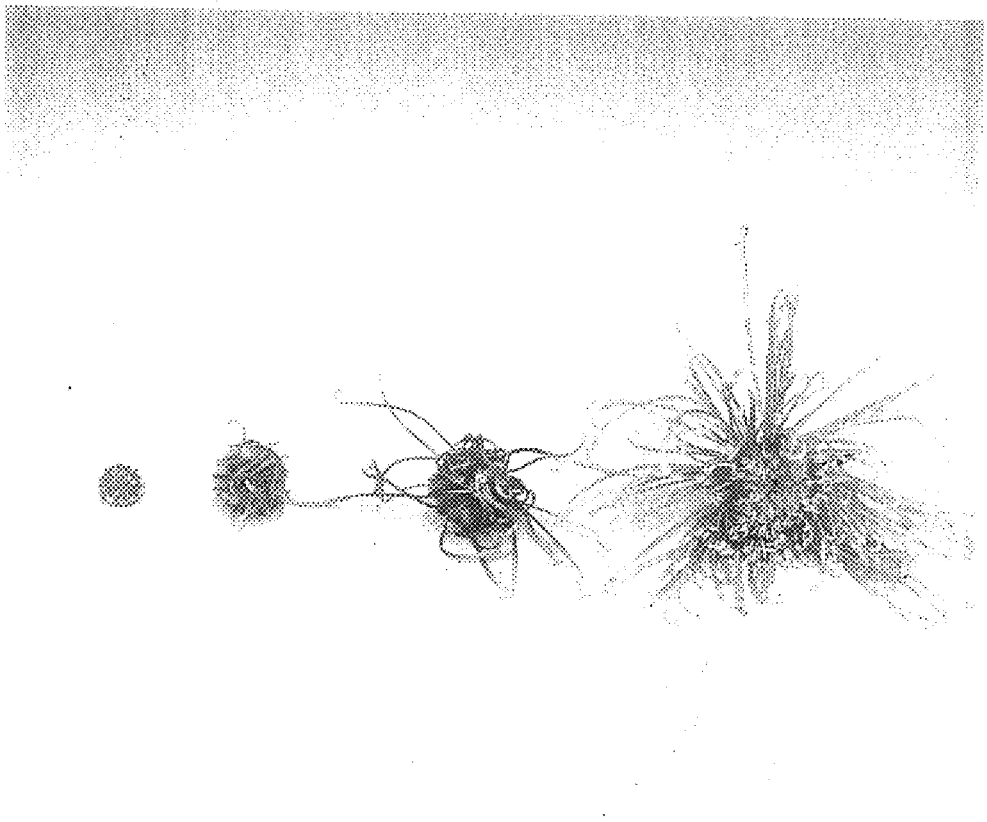
FIG. 2 shows the various stages of bloom of the new cultivar.
Figure 3:
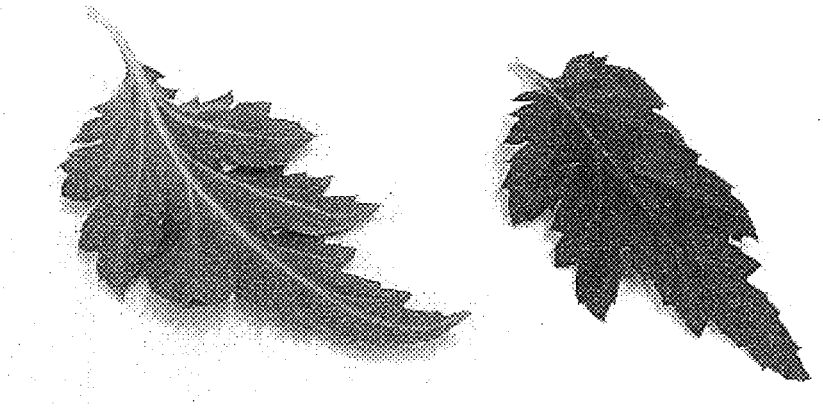
FIG. 3 shows the foliage of the new cultivar.

This new variety of *Chrysanthemum* is of the botanical classification *Chrysanthemum morifolium*. The observations and measurements were gathered from plants grown in Rijsenhout Holland in a photo-periodic controlled crop under conditions generally used in commercial practice. The greenhouse temperatures during this crop were at day-time between 18° C. and 25° C. and at night 20° C. After a long day period of 14 days the photo-periodic response time in this crop was 56 days. After the long day period to flowering growth retardants were applied 2 to 3 times in an average dose of 2.5 gram/liter water. The plants were observed (directly) during the flowering of this crop. When slightly damaged during harvest, the ray florets have proven to be sensitive to botrytis. No tests were done on disease or insect resistance or susceptibility. No tests were done on cold or drought tolerance. This new variety produces large sized inflorescences with elongated quilled pink ray-florets blooming on the plant for 5 weeks. This new variety of *Chrysanthemum* has been found to retain its distinctive characteristics throughout successive propagations however the phenotype may vary significantly with variations in environment such as light intensity and temperature. To show the phenotype as described 'Kiko' can be planted without assimilation lightning (high pressure sodium lamps) between week 4 and week 32 under greenhouse conditions in Holland. With assimilation light (minimum level 2500 lux) it can be planted year round under greenhouse conditions in Holland.

From the cultivars known to inventor the most similar existing cultivar in comparison to 'Kiko' is 'Dance' (U.S. Plant Pat. No. 12,941). When 'Dance' and 'Kiko' are being compared the following differences and similarities are noticed. Both 'Dance' and 'Kiko' are typically grown as disbud varieties, producing large sized blooms with elongated quilled ray florets. The differences of 'Dance' and 'Kiko' are (1) Size inflorescence. The size of the bloom of 'Dance' is smaller than that of 'Kiko'. (2) Length ray floret. The ray florets of 'Dance' are shorter in length than those of 'Kiko'. (3) Color ray florets. The ray florets of 'Dance' are purple colored, while those of 'Kiko' are pink.

The following is a description of the plant and characteristics that distinguish 'Kiko' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, edition 1995.

TABLE 1

| Botanical Description of cultivar 'Kiko' | |
|---|---|
| Bud | |
| Size | Large, cross-section 1.5 cm height 1.5 cm |
| Outside color | Yellow-green 145A |
| Involucral bracts | 3 rows, length 1 cm, width 1.5 cm |
| Involucral bracts among disc-florets | Not present |
| Involucral bracts color | Green 138B |
| Inflorescences | |
| Type | Double |
| Height | 5 cm |
| Size | Large |
| Fully expanded | 19 cm |
| Number per stem | 1 (typically grown as disbud) |
| Performance on the plant | 3 weeks |
| Seeds | Seed production not observed |
| Fragrance | Typical *chrysanthemum,* slight |
| Peduncle length | 3 cm |
| Peduncle color | Green 138C |
| Color | |
| Center of the flower | Immature Yellow-green 150D<br>Mature Yellow-green 144D |
| Color of the ray-florets | Upper surface Red-purple 65B<br>Lower surface Red-purple 65B |
| Tonality from Distance | A disbudded mum with pink flowers and a cream disc |
| Color of the upper surface of the ray-florets after aging of the plant | Red-purple 65B |
| Ray florets | |
| Texture | Upper and under side smooth |
| Number | 200 |
| Shape | Elongated quilled |
| Longitudinal axis of majority | Straight to incurving |
| Length of corolla tube | 8 cm |
| Ray-floret margin | Entire |
| Ray-floret length | 9 cm |
| Ray-floret width | 0.2 cm |
| Ratio length/width | High |
| Shape of tip | Incurved |
| Disc florets | |
| Disc diameter | 1 cm |
| Distribution of disc florets | Few, only visible at mature stages of flowering. |
| Shape | Tubular |
| Color | Yellow-green 154D blending to yellow-green 150D at tip in immature stage, and yellow-green 144D in mature stage |
| Receptacle shape | Domed raised |
| Reproductive Organs | |
| Stamen | Present in disc florets only |
| Stamen color | Yellow-green 144 B |
| Pollen | Produced in small quantities |
| Pollen color | Yellow 7A |
| Styles | Present in both ray and disc florets |
| Style color | Yellow 13A |
| Style Length | 4 mm |
| Stigma color | Yellow-green 145 D |
| Stigma Width | 1 mm |
| Ovaries | Enclosed in perianth |

TABLE 1-continued

| Botanical Description of cultivar 'Kiko' | |
|---|---|
| Plant | |
| Form | A disbudded mum meant for erect culture |
| Growth habit | Upright |
| Growth rate | Medium vigor |
| Height | 1 m |
| Width | 30 cm |
| Internode length | 2.5–3 cm |
| Spray formation | Not formed when grown as disbud |
| Stem Color | Yellow-green 148C |
| Stem Strength | Strong |
| Stem Brittleness | Not brittle |
| Stem Anthocyanin coloration | Absent |
| Flowering Response (photo-periodic controlled crop, not natural season) | 56 days |
| Foliage | |
| Color immature stage | Upper side Yellow-green 147B<br>Under side Yellow-green 148C |
| Color mature stage | Upper side Yellow-green 147A<br>Under side Yellow-green 148B |
| Color midvein mature leaf | Upper side Green 138C<br>Under side Green 139C |
| Size | Large; length 15–17 cm, width 7–9 cm |
| Quantity (number per single stem) | 30 |
| Shape | Cordiform |
| Texture upper side | Fleshy and glabrous |
| Texture under side | Pubescent |
| Venation arrangement | Palmate |
| Shape of the margin | Dentate |
| Shape of Base of Sinus Between Lateral Lobes | Acute |
| Margin of Sinus Between Lateral Lobes | Converging |
| Shape of Base | Truncate |
| Apex | Mucronulate |
| Petiole Length | 1.5–3 cm |
| Petiole Color | Green 138C |

TABLE 2

Differences of 'Kiko' with comparison variety 'Dance'

| | 'Kiko' | 'Dance' |
|---|---|---|
| Size inflorescence | 19 cm | 13.5 cm |
| Length ray florets | 9 cm | 7 cm |
| Color ray florets | Red-purple 65B | Purple 77B to 77C |

I claim:

1. A new and distinct variety of *Chrysanthemum* plant as described and illustrated.

* * * * *